(12) United States Patent
Horn

(10) Patent No.: US 6,515,006 B2
(45) Date of Patent: Feb. 4, 2003

(54) OPHTHALMIC FORMULATION WHICH MODULATES DILATION

(75) Inventor: Gerald Horn, Deerfield, IL (US)

(73) Assignee: HMT Pharma, Inc., North Riverside, IL (US)

( * ) Notice: Subject to any disclaimer, the term of this patent is extended or adjusted under 35 U.S.C. 154(b) by 0 days.

(21) Appl. No.: 10/165,459

(22) Filed: Jun. 7, 2002

(65) Prior Publication Data

US 2002/0187986 A1 Dec. 12, 2002

Related U.S. Application Data

(62) Division of application No. 09/710,758, filed on Nov. 8, 2000, now Pat. No. 6,420,407.

(51) Int. Cl.$^7$ ............................................. A67K 31/415
(52) U.S. Cl. ....................... 514/385; 514/369; 514/603; 514/912
(58) Field of Search ................................ 514/385, 396, 514/603, 912

(56) References Cited

U.S. PATENT DOCUMENTS 4,443,441 A * 4/1984 Calin .......................... 424/244
5,885,550 A * 3/1999 Vallier ...................... 424/10.32

* cited by examiner

Primary Examiner—Zohreh Fay
(74) Attorney, Agent, or Firm—Bell, Boyd & Lloyd LLC

(57) ABSTRACT

An ophthalmic formulation is disclosed which reduces dilation in dim light and reduces redness.

26 Claims, No Drawings

OPHTHALMIC FORMULATION WHICH MODULATES DILATION

This application is a divisional of Ser. No. 09/710,758 filed on Nov. 8, 2000, now U.S. Pat. No. 6,420,407.

FIELD OF THE INVENTION

The present invention relates to a composition formulated and administered to a human eye to reduce dilation and redness.

BACKGROUND OF THE INVENTION

While it is known that pupil size varies in its diameter in darkness between individuals from 3 mm to 9 mm, little attention has been paid to the effect of this difference on the night vision and vision in dim light (scotopic vision is dark adapted vision). Those with large pupils suffer from much more light scatter, glare, halo, and related aberrant focus of light rays that can make function under certain conditions of lighting very difficult.

Laser vision correction in particular has added new quality of vision difficulties for many of these individuals. Exposing the retina to light focusing from as much as nine times more surface area essentially magnifies every variation in curvature from the ideal. Currently, only direct acting miotic agents such as pilocarpine are used in an effort to decrease pupil size.

Pilocarpine causes brow ache, ciliary muscle contraction and pseudo myopia, excessive dimness when first applied, and redness. Its effect lasts only a few hours, and it has known, though remote, risk of retinal detachment probably related to pull on the retina from stimulated ciliary muscle contraction. For these reasons it is rarely tolerated or considered a clinically useful alternative for patients with large pupils in dim light.

Another medication used to affect pupil size is dapiprazole, an alpha-1 adrenergic receptor blocking agent. Dapiprazole is 5,6,7,8-tetrahydro-3-[2-(4-o,tolyl-1-piperazinyl)ethyl]-8-triazolo[4,3-a]pyridine hydrochloride. It is available in a 0.5% solution to partially counteract, or reverse, the dilation effect of phenylephrine, an adrenergic dilating agent, and the dilating and accommodation loss caused by tropicamide. In addition to producing redness upon instillation, dapiprazole has very little effect on pupil size in dim light in clinical application when used topically for this purpose, and therefore its sole use is as a treatment of iatrogenically induced mydriasis produced by adrenergic or parasympatholytic agents.

SUMMARY OF THE INVENTION

An ophthalmic formulation of the invention preferably obtains two simultaneous effects (a) reducing the amount of dilation the eye would normally undergo in a low light environment; and (b) reducing eye redness. Reducing normal dilation can be obtained by administering a compound which interferes with the normal stimulation of muscles which cause dilation. This can be done, for example, with an alpha 1 antagonist. However, redness may be reduced using an alpha 1 agonist. The antagonist and agonist will, in general, counteract each other. The present invention provides a particularly preferred formulation of (a) an alpha 1 antagonist which is phentolamine; and (b) an alpha 1 agonist which is tetrahydrozoline and specifically tetrahydrozoline hcl. This combination reduces dilation and redness.

A formulation for optimizing pupil size in extreme lighting conditions is disclosed. The formulation is preferably a solution of the type used in an artificial tear formulation having dissolved therein a therapeutically effective amount of a compound characterized by its ability to reduce dilation of the eye, particularly in dim light. The compound generally interferes with a natural biochemical reaction which results in the stimulation of the dilator muscles of the eye. The formulation is preferably further comprised of a compound which reduces eye redness, e.g. tetrahydrazolene. The compound which has the ability to disrupt endogenous compounds which stimulate dilator muscles of the eye may be an alpha 1 antagonist which belongs to a class of compounds with phentolamine or phenoxybenzamine groups.

A method of optimizing pupil diameter is disclosed wherein the pupil diameter in dim light is effected so that it is not more than 200% greater than its size in bright light. The method encompasses administering a therapeutically effective amount of an alpha 1 antagonist to an eye of a person in need thereof. The optimized pupil diameter in dim light may be no more than 5 mm, and the pupil diameter in bright light may be constricted no more than 1 mm. Further, the optimized pupil diameter in dim light may be between and including 3 mm and 5 mm and will vary with different patients. Actual results with human patient's are shown in the Examples.

In accordance with the method of the invention an application device such an eyedropper is utilized in order to apply a therapeutically effective amount of an alpha 1 agonist to the eye of a patient which is preferably the eye of a human patient. Thereafter, the formulation is allowed to effect the pupil of the eye and contract the pupil so that the pupil does not expand above a level which is twice the level of dilation when the eye of the patient is present in bright light. Accordingly, another aspect of the invention is a formulation comprised of an aqueous solution having an alpha 1 agonist present therein wherein the formulation is present in an eyedropper.

The present invention is also directed to a method for optimizing pupil diameter in dim light by minimizing its dilatation in response to less light, comprising administering a therapeutically effective amount of an alpha 1 antagonist to an eye of a person in need thereof. In this method, dilatation of the pupil diameter in dim light may be minimized in response to less light compared with bright light, and the method may not induce ciliary muscle contraction.

In the method of the present invention, the patient may suffer from excessively large pupils in dim light, and the patient may suffer from poor quality of vision, and the patient may be undergoing medication that results in dilatation of the pupil diameter. Alternatively, the pupil diameter of the patient may be naturally excessively dilated as a result of response to dimming of light.

The method of the invention may be carried out by directly instilling onto the eye an eye drop formulation of the invention. Optionally, the alpha 1 antagonist may be administered by contacting a contact lens, and the contact lens applied to the eye. In the method of the invention, the used alpha 1 antagonist preferably may belong to a class of compounds belonging to the phentolamine or phenoxybenzamine groups.

The present invention is directed to a method for reducing pupil diameter in dim light in cases where dilation of the pupil is excessive, such as 6 mm or greater. Administering a formulation of the invention does not induce ciliary contraction or undesirable pseudomyopia that may result from taking certain medication. Formulations disclosed here reverse mydriasis of parasympatholytic agents. Formulations of the invention are effective on agents paralyzing accommodation such as 1% cylogyl, which can then be used for more complete cycloplegia and accurate prelaser refractive measurement.

There are no generally available eye drops for optimizing pupil size such as by reducing pupil diameter in dim light without undesirable side effects. The present invention recognizes that the alpha-1 antagonists which are currently used for treatment of high blood pressure, treatment of pheochromocytoma, migraines, bladder spasm, prostate enlargement, and sexual dysfunction can be formulated used in reducing pupil diameter.

The present invention provides an ophthalmic composition which achieves the combined requirements of comfort and pupil diameter optimization.

Alpha adrenergic receptor antagonists function to block alpha-1 receptor mediated contraction of arterial and venous smooth muscle. Alpha-2 adrenergic receptors are involved in suppressing sympathetic output, increasing vagal tone, facilitating platelet aggregation, inhibiting the release of norepinephrine and regulating metabolic effects. Alpha adrenergic antagonists have a wide spectrum of pharmacological specificities and are chemically heterogeneous.

Alkylating agents, imidazolines, piperazinyl quinazolines and indoles comprise the various chemical classes of alpha receptor antagonists. Many have both alpha-1 and alpha-2 receptor antagonist activity. For the present invention alpha-2 activity as represented by the indoles is of no clinical benefit. The alkylating agents offer potential for long term effectiveness for minimizing pupillary dilation, but are less effective and cause more redness than the imidazolines, such as phentolamine. The piperazinyl quinazolines, such as prazosin and dapiprazole, have a modest effect on pupil diameter in dim light, but to date our research shows they are not as clinically effective as the imidazolines for this purpose. Development of longer lasting, more potent piperazinyl quinazolines may be clinically effective however. As phentolamine is not as strong an alpha-1 receptor antagonist as prazosin its stronger clinical benefit may relate to other related properties of the drug as well as its alpha-1 antagonism. These properties include blocking receptors for 5-HT, release of histamine from mast cells, and blockage of K+ channels. Phenoxybenzamine is similar in its chemical mediation.

An aspect of the invention is an ophthalmic formulation comprised of an aqueous solvent and an alpha 1 antagonist. The aqueous solvent may, in its simplest form, be water but is preferably a solvent comprised of an ophthalmic artificial tear solution. The alpha 1 antagonist is preferably present in a relatively low concentration e.g. less than 1% concentration. For example, the alpha 1 antagonist may be present in an amount in the range of 0.01 milligram per cubic centimeter of aqueous solvent to about 50 milligram per cubic centimeter of solvent. Another aspect of the invention is the formulation of the invention present within an application device such as a conventional or improved eyedropper of the type described herein.

An advantage of the invention is that it can be utilized to treat patients who have been subjected to laser surgery and have developed a range of different vision problems as a result of excessive dilation of their pupils.

A feature of the invention is that the alpha 1 antagonist can be formulated in a manner which is readily administered to the eye to obtain a desired effect.

These and other aspects, advantages and features of the invention will become apparent to those skilled in the art upon reading this disclosure.

DETAILED DESCRIPTION OF THE INVENTION

Before the present formulations and methods are described, it is to be understood that this invention is not limited to particular compounds, formulas or steps described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a compound" includes a plurality of such compounds and reference to "the step" includes reference to one or more step and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

CHARACTERISTICS OF THE EYE

It is well known that pupillary dilation in dim light is a teleologic adaption to allow more light to enter our eyes. Along with adaptions on the retina to scotopic, or night vision, this allows increased useful acuity over a very large range of lighting in low lit situations. Less well known is the dramatic range that exists among human beings of the degree to which pupils will dilate in dim light, ranging from maximal dilation in complete darkness of as little as 3 mm in some individuals to as high as 9 mm in others. This difference is part of the genetic makeup of an individual.

When living in literal total darkness there may have been a very slight advantage to having larger pupil diameters in dim light, but whatever advantage was conferred has been lost once several advances in civilization resulted in illumination; including artificial means of background lighting, neon lights to allow signs to be more easily read, fluorescent light with its weighted blue more highly scattering component, and point sources of light caused by car headlights and traffic lights. These light sources are visible at optimal quality when sufficient corneal diameter exists to allow light to enter, such as a 3 mm pupil, but less corneal diameter is used to refract light, as less light scatter is induced than 5–6 millimeters pupils or larger. The preferred optimized pupil size in dim light according to the present invention is about 3–5 millimeters, more preferably 4–5 millimeters.

The peripheral corneal curvature in many people is not in perfect curvature alignment with that of the central cornea. In individuals with small to moderate pupils in dim light the pupil acts as a filter so that the peripheral cornea in these cases is not a factor. But, for larger pupils in dim light, peripheral corneas may be either too steep or too flat in many cases relative to the central curvature, causing spherical aberration. These corneas are technically referred to as either prolate or oblate when imperfect. The eye drops of the present invention clinically eliminate virtually all such spherical aberration, as the peripheral corneal curvature outside of a central 4–5 mm optical zone are filtered by the treated smaller pupil in dim light and the extraneous light focused by the spherical aberration is eliminated.

Three millimeter pupils are sufficiently large to allow sufficient light to enter the eye in scotopic situations, yet provide excellent filters to minimize light scatter of ambient artificial light and or point sources of light. Nine millimeter pupils on the other hand, utilizing nine times more corneal surface area, induce considerable light scatter of point sources, neon lights, and fluorescent blue light. While the current state of the art within the ophthalmic and optometric professions does not generally recognize this distinction, and wherein refractive surgery standard of care does not generally recognize a distinction in pupil diameter in dim light as a predictive factor in outcome, use of the novel pharmacologic method of the present invention has demonstrated this to be so in clinical use. Tables 1 and 2 demonstrate the results of a study of several different alpha adrenergic antagonists on several patients, with different parameter being measured.

Refractive optical aids such as glasses or contact lenses increase the degree of light scatter in scotopic situations by adding optical elements that are imperfect in that they have surfaces that scatter light. Refractive surgery on the cornea, whereby a change in contour is induced by surgical means that can include incision (RK), laser ablation (Lasik, PRK), or prosthesis (plastic segments inserted into the cornea) also adds imperfections that increase the degree of light scatter in scotopic conditions. The variables of pupil size in dim light and refractive optics adding to light scatter has created circumstances in which individuals have quality of vision difficulty navigating in scotopic situations as a result of glare, halo, and related distortions at night or in dimly lit environments of any kind.

The invention is particularly useful in treating patients who have been subjected to various types of refractive surgery as described above. Because such surgery can increase the degree of light scatter the administration of the formulation of the invention can modulate this effect by contracting the pupil. Thus, the invention includes carrying out refractive surgery on a patient and thereafter administering a formulation of the invention to the patient over time as needed e.g. to maintain the pupil size at about 3–5 mm, preferably 4–5 mm. The formulation of the invention may be administered periodically on a daily basis (twice daily or as needed) and particularly administered in situations where the patient is subjected to dim light.

The term "dim light" is used herein to refer to a light environment wherein the pupils of the patient are dilated to a substantially maximum amount. Alternatively, the term "bright light" is used herein to describe a surrounding light environment wherein the pupil of the patient's eye is contracted maximally i.e. dilated to a minimum amount. An aspect of the present invention is that the formulation can reduce the differential in pupil dilation and in particular reduce the dilation of the patient's pupil to an amount of 200% or less in dim light as compared to the amount of dilation which would occur in bright light.

The method of the invention utilizes a novel pharmacologic means of optimizing pupil size by reducing pupil size in dim light. Conventional teaching of eye specialists has been to use constricting agents of the pupil, such as acetylcholine or cholinesterase inhibitors to reduce pupil size. Using dilute concentrations of such agents it is possible to constrict the pupil and create improved viewing for affected individuals in scotopic environments. However, undesirable side effects of such medications, including excessive constriction initially causing severe dimming, brow ache, generalized pain, redness, and induced blurring secondary to ciliary accommodation, severely limits the value of these classes of pharmacologic agents. Retinal detachment is a known rare complication of its use.

PHARMACEUTICALLY ACTIVE COMPONENT

The pharmacologic method of the present invention utilizes a class of compounds known as alpha 1 antagonists to inhibit pupillary dilation in scotopic conditions preferentially over constriction of the pupil, affecting the dilator muscles of the iris preferentially, and has no clinically significant effect on the ciliary muscle responsible for accommodation. This class of compounds has been used to treat hypertension, prevent bladder spasmodic contractions and improve urinary outflow, and treat prostate enlargement. While toxic levels of alpha 1 antagonists are known to cause pinpoint pupils, no formulation has previously been developed as a topical pharmaceutical agent to limit dilation of the iris.

A significant feature of the present invention is to employ more potent alpha antagonists, particularly alpha 1 antagonists, to allow improvement in quality of vision in dim light without negative clinical effects in normal lighting conditions. Additionally, another feature of the present invention is to reverse the effects of parasympatholytics more effectively than dapiprazole.

The composition of the present invention can be used to optimize pupil size to obtain enhanced vision acuity in dim light by reducing the pupil diameter in dim light, but which does not clinically substantially reduce the pupil size in bright light, when the pupil size does not require it to be treated to reduce the pupil size to the same extent as the pupil under dim light.

According to the invention, the optimized pupil diameter in dim light is no more than 200% greater than that in bright light. Preferably, the pupil diameter in dim light is no more than 150%, more preferably, 100%, even more preferably, 75%, still more preferably, 60%, still more preferably, 50%, and most preferably, 33% greater than that in bright light.

While the composition of the present invention can be used to optimize pupil size under any circumstances, the composition of the invention is administered to the eye of an individual to reduce naturally occurring pupillary dilation in dim light, especially in situations where the dilation is excessive to affect vision acuity. The composition of the invention can be used also to counteract pupil dilatation caused by medication.

As used in the present application, alpha 1 antagonist refers to any agent that binds to the alpha 1 adrenergic receptor, which includes alpha 1 adrenergic receptor antagonist. Preferably, the alpha 1 adrenergic receptor is iris smooth muscle dilator selective. More preferably, the alpha 1 antagonist is in the phentolamine family, known as imidazolines, an alkylating agent such as phenoxybenzamine, or a piperazinyl quinazoline with more potent alpha-1 adrenergic antagonist activity than dapiprazole. Most preferably, the alpha 1 antagonist of the invention is phentolamine or phenoxybenzamine, but any alpha 1 antagonist can be used in the present invention.

Alpha 1 antagonists such as phentolamine or phenoxybenzamine. These compounds are currently used to treat pheochromocytoma, a condition in which alpha receptor stimulants such as epinephrine and norepinephrine are released throughout the body in extremely high concentration. Examples of alpha 1 antagonist are disclosed within issued U.S. Pat. No. 6,046,207 issued Apr. 4, 2000. Other examples are disclosed within U.S. Pat. Nos. 5,891,882 and 5,792,767. The above cited three U.S. patents are incorporated herein by reference to disclose alpha 1 antagonist. Further, publications cited in these patents are incorporated herein by reference in order to disclose and describe therapeutically effective compounds which can be formulated and used in connection with the present invention when used in appropriate ophthalmic formulations and applied directly to the eye of a patient to effect pupil dilation.

FORMULATIONS—DOSAGE

According to the invention, an ophthalmic composition containing an alpha 1 antagonist is advantageously applied topically to the eye, especially in the form of a solution, a suspension, an ointment, a gel or a solid insert. Such compositions comprise the active ingredient, for example, in a range of from approximately 0.01 milligrams per cc to approximately 50 milligrams per cc, preferably from approximately 0.05 milligrams per cc to approximately 20 milligrams per cc, or more preferably in the range of from approximately 0.1 milligrams per cc to approximately 10 milligrams per cc and most preferably in the range of from 1 milligram per cc to 5 milligrams per cc. The dose of the active ingredient may depend on various factors, such as mode of administration, requirement, age and/or individual condition.

A preferred concentration of 3.3 milligrams per cc is administered by placing a single drop on a moist soft contact lens, and inserting the lens for 15–45 minutes, 1× per day. Administered in this manner the drop has a 20–24 hour clinical effectiveness, and in fact appears to have cumulative affect, such that with regular usage an every other day administration via the contact lens may be all that is necessary for some patients. The contact lens dosing allows for preferential absorption within the cornea, maximizing drop utilization and minimizing mild redness that may otherwise occur as well as the remote risk of systemic absorption. The amount of phentolamine within 1 drop—less than 0.33 mg—is about 15× less than the clinically recommended dosing for testing within the body. Of this it is unlikely as much as 10% would ever reach the systemic circulation, resulting in 150× less than a typical clinical dosage. Using contact lens dosing this is estimated to be still 10× less, or 1500 times less than a typical clinical dosage. The drop may be administered in a 3.3 milligram per cc concentration directly to the eye as a recommended daily or BID dosing.

An effective drop for the purpose of the present invention, because it limits pupil dilation and does not significantly affect pupillary constriction should have significantly more effect and cause significantly increased percentage reduction in pupil diameter in patients with large pupils in dim light, whose dim light pupil exceeds their daylight pupil considerably, and much less effect on pupil diameter in patients who have a more idealized pupil diameter in dim light, where their dim light pupil is nearly equal to their daylight pupil. This is in fact the case with phentolamine as administered (see Table 2).

There are used for a corresponding ophthalmic composition customary pharmaceutically acceptable excipients and additives known to the person skilled in the art, for example those of the type mentioned below, especially carriers, stabilizers, solubilizers, tonicity enhancing agents, buffer substances, preservatives, thickeners, complexing agents and other excipients. Examples of such additives and excipients can be found in U.S. Pat. Nos. 5,891,913, 5,134,124 and 4,906,613. Such compositions are prepared in a manner known, for example by mixing the active ingredient with the corresponding excipients and/or additives to form corresponding ophthalmic compositions. The active ingredient is preferably administered in the form of eye drops, the active ingredient being conventionally dissolved, for example, in a carrier. The solution is, where appropriate, adjusted and/or buffered to the desired pH and, where appropriate, a stabilizer, a solubilizer or a tonicity enhancing agent is added. Where appropriate, preservatives and/or other excipients are added to an ophthalmic composition.

Carriers used in accordance to the present invention are typically suitable for topical or general administration, and are for example water, mixtures of water and water-miscible solvents, such as $C_1$- to $C_7$-alkanols, vegetable oils or mineral oils comprising from 0.5 to 5% by weight hydroxyethylcellulose, ethyl oleate, carboxymethylcellulose, polyvinylpyrrolidone and other non-toxic water-soluble polymers for ophthalmic uses, such as, for example, cellulose derivatives, such as methylcellulose, alkali metal salts of carboxymethylcellulose, hydroxymethylcellulose, hydroxyethylcellulose, methylhydroxypropylcellulose and hydroxypropylcellulose, acrylates or methacrylates, such as salts of polyacrylic acid or ethyl acrylate, polyacrylamides, natural products, such as gelatin, alginates, pectins, tragacanth, karaya gum, xanthan gum, carrageenin, agar and acacia, starch-derivatives, such as starch acetate and hydroxypropyl starch, and also other synthetic products, such as polyvinyl alcohol, polyvinylpyrrolidone, polyvinyl methyl ether, polyethylene oxide, preferably cross-linked polyacrylic acid, such as neutral Carbopol, or mixtures of those polymers. Preferred carriers are water, cellulose derivatives, such as methylcellulose, alkali metal salts of carboxymethylcellulose, hydroxymethylcellulose, hydroxyethylcellulose, methylhydroxypropylcellulose and hydroxypropylcellulose, neutral Carbopol, or mixtures thereof. The concentration of the carrier is, for example, from 1 to 100,000 times the concentration of the active ingredient.

The solubilizers used for an ophthalmic composition of the present invention are, for example, tyloxapol, fatty acid glycerol poly-lower alkylene glycol esters, fatty acid poly-lower alkylene glycol esters, polyethylene glycols, glycerol ethers vitamin E and vitamin E derivatives, such as Vitamin E Tocopherol Polyethylene Glycol 1000 Succinate (TPGS) or mixtures of those compounds. A specific example of an especially preferred solubilizer is a reaction product of castor oil and ethylene oxide. Reaction products of castor oil and ethylene oxide have proved to be particularly good solubilizers that are tolerated extremely well by the eye. Another preferred solubilizer is tyloxapol. The concentration used depends especially on the concentration of the active ingredient. The amount added is typically sufficient to solubilize the active ingredient. For example, the concentration of the solubilizer is from 0.1 to 5000 times the concentration of the active ingredient.

According to the present invention lower alkylene means linear or branched alkylene with up to and including 7 C-atoms. Examples are methylene, ethylene, 1,3-propylene, 1,2-propylene, 1,5-pentylene, 2,5-hexylene or 1,7-heptylene. Lower alkylene is preferably linear or branched alkylene with up to and including 4 C-atoms.

Examples of buffer substances are acetate, ascorbate, borate, hydrogen carbonate/carbonate, citrate, gluconate, lactate, phosphate, propionate, perborate and TRIS (tromethamine) buffers. Tromethamine and borate buffer are preferred buffers. The amount of buffer substance added is, for example, that necessary to ensure and maintain a physiologically tolerable pH range. The pH range is typically in the range of from 5 to 9, preferably from 6 to 8.2 and more preferably from 6.8 to 8.1.

Tonicity enhancing agents are, for example, ionic compounds, such as alkali metal or alkaline earth metal halides, such as, for example, $CaCl_2$, KBr, KCl, LiCl, NaI, NaBr or NaCl, or boric acid. Non-ionic tonicity enhancing agents are, for example, urea, glycerol, sorbitol, mannitol, propylene glycol, or dextrose. For example, sufficient tonicity enhancing agent is added to impart to the ready-for-use ophthalmic composition an osmolality of approximately from 50 to 1000 mOsmol, preferred from 100 to 400 mOsmol, more preferred from 200 to 400 mOsmol and even more preferred from 280 to 350 mOsmol.

Examples of preservatives are quaternary ammonium salts, such as cetrimide, benzalkonium chloride or benzoxonium chloride, alkyl-mercury salts of thiosalicylic acid, such as, for example, thiomersal, phenylmercuric nitrate, phenylmercuric acetate or phenylmercuric borate, parabens, such as, for example, methylparaben or propylparaben, alcohols, such as, for example, chlorobutanol, benzyl alcohol or phenyl ethanol, guanidine derivatives, such as, for example, chlorohexidine or polyhexamethylene biguanide, or sorbic acid. Preferred preservatives are cetrimide, benzalkonium chloride, benzoxonium chloride and parabens. Where appropriate, a sufficient amount of preservative is added to the ophthalmic composition to ensure protection against secondary contaminations during use caused by bacteria and fungi.

The ophthalmic compositions may comprise further non-toxic excipients, such as, for example, emulsifiers, wetting agents or fillers, such as, for example, the polyethylene glycols designated 200, 300, 400 and 600, or Carbowax designated 1000, 1500, 4000, 6000 and 10,000. Other excipients that may be used if desired are listed below but they are not intended to limit in any way the scope of the possible excipients. They are especially complexing agents, such as disodium-EDTA or EDTA, antioxidants, such as ascorbic acid, acetylcysteine, cysteine, sodium hydrogen sulfite, butyl-hydroxyanisole, butyl-hydroxytoluene or .alpha.-tocopherol acetate; stabilizers, such as a cyclodextrin, thiourea, thiosorbitol, sodium dioctyl sulfosuccinate or monothioglycerol vitamin E and vitamin E derivatives, such as Vitamin E Tocopherol Polyethylene Glycol 1000 Succinate (TPGS); or other excipients, such as, for example, lauric acid sorbitol ester, triethanol amine oleate or palmitic acid ester. Preferred excipients are complexing agents, such as disodium-EDTA and stabilizers, such as a cyclodextrin. The amount and type of excipient added is in accordance with the particular requirements and is generally in the range of from approximately 0.0001 to approximately 90% by weight.

In another embodiment of the present invention, the ophthalmic composition comprises a therapeutically effective amount of alpha 1 antagonist, a carrier, a solubilizer and another therapeutically effective pharmaceutical agent which may be, for example, an antibiotic, an antiallergic, an anesthetic, or another drug.

A range of different alpha 1 antagonists are known to those skilled in the art. The present invention is intended to encompass such compounds and equivalent compounds which have substantially the same therapeutic effect as the present invention. Specifically, the present invention is intended to encompass formulations which comprise an aqueous solvent having dissolved therein a therapeutically effective amount of a compound which compound when dissolved in the formulation in a low concentration (1% or less) and administered to a human patient's eye will prevent dilation of the eye in dim light to a level which is about twice the amount of dilation or less than occurs when the patient is present in bright light.

ARTIFICIAL TEARS

As indicated above a simple formulation of the present invention comprises an aqueous solvent which may be sterile water suitable for administration to the eye having an alpha 1 antagonist dissolved therein in a low concentration, e.g. 1% concentration or less. However, preferred formulations of the present invention are comprised of alpha 1 antagonist dissolved in a formulation which is referred to in the art as an artificial tear formulation. Such formulations are disclosed and described within U.S. Pat. Nos. 5,895,654; 5,627,611; and 5,591,426 as well as patents and publications cited and referred to in these patents, all of which are intended to be incorporated herein by reference.

Artificial tear formulations of the invention promote good wettability and spread. Further, the artificial tear formulations preferably have good retention and stability on the eye and do not cause significant discomfort to the user . A preferred artificial tear composition of the invention, comprises (1) polyvinylpyrrolidone, preferably in the amount of about 0.1–5% by weight of said solution;

(2) benzalkonium chloride, preferably in an amount of about 0.01–0.10% by weight;

(3) hydroxypropyl methylcellulose, preferably in an amount of about 0.2–1.5% by weight of said solution; and (4) glycerin, preferably in an amount of about 0.2–1.0% by weight of said solution, wherein the composition is an aqueous solution having isotonic properties.

Those skilled in the art will recognize that a wide range of different formulations and artificial tear formulations which can be utilized in connection with the present invention.

EYEDROPPERS

Formulations of the present invention can be administered in accordance with means generally known to those skilled in the art. Generally, the formulation is administered using an eyedropper. The eyedropper may be a conventional eyedropper which is comprised of a hollow cylindrical barrel having a first end and a second end and an inner surface. Further, the eyedropper will be further comprised of a means for providing suction to draw the formulation of the invention into the hollow cylindrical barrel. The first end of the barrel is configured to receive the means for providing suction to draw in a formulation. The second end of the barrel is generally configured to have a small opening which permits passage of the formulation and allows drops of the formulation to be metered out directly onto the patient's eye. The cylindrical barrel is preferably designed so that it is relatively small and contains less than 5 cubic centimeters of formulation.

It may be desirable to utilize a measured dose eyedropper of the type described within U.S. Pat. No. 5,514,118 or an illuminated eyedropper device of the type described in U.S. Pat. No. 5,584,823. A range of other eye droppers can also be utilized of the type described within the following U.S. Pat. Nos. 5,059,188; 4,834,727; 4,629,456; and 4,515,295. The patents cited here which disclose eyedroppers are incorporated herein by reference as are the various patents and publications cited and discussed within these patents.

EXAMPLE 1

A 5 mg/ml vial of phentolamine was diluted in an artificial tear formulation to approximately 1.5 cc of solution. The artificial solution created an effective composition for reducing the pupillary diameter in dim light via topical instillation as an eye drop. This method induces mild conjunctival and episcleral blood vessels causing very slight redness to the eye.

EXAMPLE 2

The composition of Example 1 is applied as a single drop to a moist soft contact lens with no excess saline, and the medication is delivered topically over an optional 15 minute to 2 hour period, 30 minutes preferred, through wear of the soft contact lens after which time it is removed. This greatly reduces any systemic absorption of the medication, vasodilation of the vessels and minimizes redness as a result, while allowing efficient drop utilization with the most effective concentrations to reach the iris dilator muscles and minimize dilation in scotopic conditions. The loss of muscle tone of these muscles may result in very slight constriction of the pupil as well, but not sufficient to cause the dimness from a pinpoint pupil effect commonly seen with acetylcholine or cholinesterase inhibitors. There is no noticeable effect on accommodation.

Phenoxybenzamine has the advantage of creating a longer lasting alpha 1 chemical sympathectomy, reducing the frequency of application required to maintain effective scotopic viewing. Phenoxybenzamine as modified and applied requires a single instillation per day to render up to 20 to 24 hours of effect. Phenoxybenzamine formulations ranging from 0.1% to 5% have not been as effective as phentolamine, and induce much more vasodilation and congestion. Similarly, prazosin and tolamine at 0.1% to 5% exhibits slight pupillary reduction in dilation in dim light but appears to be less effective than phentolamine. Labetalol, a potent beta adrenergic receptor antagonist, consists of four isomers, two of which have some alpha-1 antagonist activity. Its S,S and S,R isomers, and in concentrations of 0.1% to 2%, 0.5% preferred, are modestly effective. Other alpha-1 antagonists such as tamsulosin, bunazosin, alfuzonsin, urapidil, ketanserin, and indoramin, in concentrations of 0.1% to 2%, with 0.5% preferred are expected to have some clinical effectiveness as well. Alpha-2 receptor antagonists, such as found in Yohimbe extract, have no effect on pupil dilation in dim light.

Neuroleptic agents such as chlorpromazine, and ergot alkaloids such as ergotamine have mild alpha-1 receptor antagonist activity and may exhibit mild effectiveness for the purposes of the present invention.

TABLE 1

Effect of Alpha Adrenergic Receptor Antagonists on Pupil Dilation

| Compound | Adrenergic receptors blocked | Effect on pupil diam. in darkness (mm) | Redness (direct topical instillation) | Duration (hrs) | Concentration |
|---|---|---|---|---|---|
| Phentolamine | α-1 | 7.5 -> 4.0 | + | 20–40 | 3.3 mg/ml* |
| Phenoxybenzamine | α-1 | 7.5 -> 5.5 | ++++ | 20–? | 5 mg/ml |
| Prazosin | α-1,2 | 7.5 -> 6 | +++ | 5–12 | 5 mg/ml |
| Dapiprazole | α-1,2 | 7.5 -> 7 | +++ | 5–12 | 5 mg/ml |
| Yohimbe | α-2 | 7.5 -> 7.5 | + | 0 | 5 mg/ml |
| Tolamine | α-1 | 7.5 -> 6 | + | 5–12 | 5 mg/ml |
| Labetalol | α-1, β | unknown | unknown | Not tested | s,r, and s,s isomers only alpha-1 antagonists |
| Bunazosin | α-1 | unknown | not avail U.S. | Not tested | |
| Tamsulosin | α-1 | unknown | not avail U.S. | Not tested | |

*applied via soft contact lens with 1–2 gtts applied and placed for 30 minutes before removed

TABLE 2

Effect of Phentolamine 0.35% on Pupil Diameter**

| Subject | Dim Light Pre mm | Bright Light Pre mm | Dim Light Post mm | Bright Light Post mm | Comments |
|---|---|---|---|---|---|
| NF | 7.0 | 3.5 | 4.0 | 3.0 | Night vision good pre and post |
| NB | 7.5 | 4.0 | 4.0 | 3.0 | Had glare,halos, poor night vision pre: post night = day = exc; glare = 0; halos 70% reduced; depth perception improved |
| LR | 7.5 | 3.0 | 4.0 | 2.5 | Had glare, halo's poor night vision pre:post night much improved, dim light about same. |
| GH | 3.5 | 3.0 | 3.0 | 2.5 | Night vision good pre and post |
| LH | 4.0 | 3.0 | 3.5 | 2.5 | Night vision good pre and post |

**Phentolamine 3.3 mg/cc applied as a single drop to a soft contact lens placed for 30 minutes. Application of drops morning or daytime.

Whereas particular embodiments of this invention have been described above for purposes of illustration, it will be evident to those persons skilled in the art that numerous variations of the details of the present invention may be made without departing from the invention as defined in the appended claims.

All of the references cited herein are incorporated by reference in their entirety.

What is claimed is:

1. A method for improving scotopic vision, comprising:
    administering to a subject's eye an amount of a first compound sufficient to inhibit pupil dilation and thereby reduce an amount of scattered light perceived by the subject wherein the compound comprises an alpha-1-antagonist and wherein the reduction of scattered light improves the scoptopic vision of the subject.

2. The method of claim 1, wherein the perceived light scattering is due to corneal aberrations on the patient's eye.

3. The method of claim 2, wherein the patient's corneal aberrations are a consequence of refractive eye surgery.

4. The method of claim 2, wherein the patient's corneal aberrations are a consequence of natural irregularities of the eye.

5. The method of claim 1, further comprising:
    administering a second compound to the patient's eye, wherein the second compound is characterized by its ability to reduce eye redness in the patient's eye while present with the first compound.

6. The method of claim 5, wherein the second compound is a Tetrahydrozoline.

7. The method of claim 6, wherein the second compound is Tetrahydrozoline HCl.

8. A method for improving scotopic vision, comprising:
    administering to a subject's eye an amount of a first compound sufficient to inhibit pupil dilation and thereby reduce an amount of scattered light perceived by the subject wherein the compound comprises an imidazoline and wherein the reduction of scattered light improves the scoptopic vision of the subject.

9. The method of claim 8, wherein the imidazoline is selected from the group consisting of: Phentolamine and Tolamine.

10. The method of claim 9, wherein the compound is Phentolamine.

11. The method of claim 8, further comprising:
    administering a second compound to the patient's eye, wherein the second compound is characterized by its ability to reduce eye redness in the patient's eye while present with the first compound.

12. The method of claim 11, wherein the second compound is a Tetrahydrozoline.

13. The method of claim 12, wherein the second compound is Tetrahydrozoline HCl.

14. A method of reducing an aberrant focus of scattered light rays in a subject's eye, comprising:
    administering to the subject's eye an amount of a first compound sufficient to inhibit pupil dilation and thereby reduce an amount of scattered light rays from entering the eye wherein the compound comprises an alpha-1-antagonist and wherein the reduction of scattered light rays reduces the aberrant focus of said scattered light rays.

15. The method of claim 14, wherein the perceived light scattering is due to corneal aberrations on the patient's eye.

16. The method of claim 15, wherein the patient's corneal aberrations are a consequence of refractive eye surgery.

17. The method of claim 15, wherein the patient's corneal aberrations are a consequence of natural irregularities of the eye.

18. The method of claim 14, further comprising:
    administering a second compound to the patient's eye, wherein the second compound is characterized by its ability to reduce eye redness in the patient's eye while present with the first compound.

19. The method of claim 18, wherein the second compound is a Tetrahydrozoline.

20. The method of claim 19, wherein the second compound is Tetrahydrozoline HCl.

21. A method of reducing an aberrant focus of scattered light rays in a subject's eye, comprising:
    administering to the subject's eye an amount of a first compound sufficient to inhibit pupil dilation and thereby reduce an amount of scattered light rays entering the eye wherein the compound comprises an imidazoline and wherein the reduction of scattered light rays reduces the aberrant focus of said scattered light rays.

22. The method of claim 21, wherein the imidazoline is selected from the group consisting of: Phentolamine and Tolamine.

23. The method of claim 22, wherein the compound is Phentolamine.

24. The method of claim 21, further comprising:
    administering a second compound to the patient's eye, wherein the second compound is characterized by its ability to reduce eye redness in the patient's eye while present with the first compound.

25. The method of claim 24, wherein the second compound is a Tetrahydrozoline.

26. The method of claim 25, wherein the second compound is Tetrahydrozoline HCl.

* * * * *